United States Patent [19]

Miyazawa et al.

[11] Patent Number: 5,120,716
[45] Date of Patent: Jun. 9, 1992

[54] PERCUTANEOUS ABSORPTION PROMOTING AGENT AND DERMATOLOGIC PREPARATION CONTAINING THE SAME

[75] Inventors: Kiyoshi Miyazawa; Tadahiro Chiba; Yuhei Iwata; Uhei Tamura; Isao Murotani; Shuya Tamaki, all of Yokohama, Japan

[73] Assignee: Shiseido Company Ltd., Tokyo, Japan

[21] Appl. No.: 298,610

[22] PCT Filed: Feb. 22, 1988

[86] PCT No.: PCT/JP88/00187
  § 371 Date: Oct. 5, 1988
  § 102(e) Date: Oct. 5, 1988

[87] PCT Pub. No.: WO88/06041
  PCT Pub. Date: Aug. 25, 1988

[30] Foreign Application Priority Data

Feb. 23, 1987 [JP] Japan .................. 62-39756
Feb. 26, 1987 [JP] Japan .................. 62-43954
Mar. 19, 1987 [JP] Japan .................. 62-65297
Mar. 19, 1987 [JP] Japan .................. 62-65298

[51] Int. Cl.⁵ .............. A61K 47/00; A61K 9/06; A61K 9/70
[52] U.S. Cl. ............ 514/23; 514/25; 514/171; 514/273; 514/109; 514/420; 514/451; 514/454; 514/518; 514/559; 514/730; 514/947; 514/975
[58] Field of Search .............. 514/77, 109, 517, 644, 514/143, 975, 556, 518, 947, 171, 273, 730, 451, 454, 23, 25, 420; 424/DIG. 4

[56] References Cited

U.S. PATENT DOCUMENTS

| | | | |
|---|---|---|---|
| 2,914,441 | 11/1959 | Zakheim | 514/975 |
| 4,329,334 | 5/1982 | Su et al. | 429/DIG. 4 |
| 4,384,974 | 5/1983 | Guthauser | 424/170 |
| 4,536,519 | 4/1985 | Wuest et al. | 514/143 |
| 4,537,772 | 8/1985 | Alexander et al. | 514/556 |
| 5,023,085 | 6/1991 | Francoeur et al. | 514/947 |

FOREIGN PATENT DOCUMENTS

| | | | |
|---|---|---|---|
| 0038512 | 10/1981 | European Pat. Off. | 47/1 |
| 0046594 | 3/1982 | European Pat. Off. | 9/10 |
| 2359165 | 2/1978 | France | 47/1 |

Primary Examiner—Mukund J. Shah
Assistant Examiner—E. C. Ward
Attorney, Agent, or Firm—Sprung Horn Kramer & Woods

[57] ABSTRACT

A percutaneous absorption promoting agent comprising (A) at least one anionic surfactant and one or two or more of surfactants having a nitrogen atom in the molecule other than anionic surfactants, (B) one or two or more of anionic surfactants and one or two or more of nonionic surfactants not having a nitrogen atom in the molecule, (C) one or two or more of surfactants selected from the group consisting of amphoteric surfactant and semi-polar surfactants and at least one nonionic surfactant having a nitrogen atom in the molecule, (D) one or two or more of surfactants selected from the group consisting of nonionic surfactants, amphoteric surfactants, semi-polar surfactants and cationic surfactants having a nitrogen atom in the molecule, and one or two or more of nonionic surfactants not having a nitrogen atom in the molecule, or (E) an amine oxide as the active ingredient, and a dermatological preparation containing these percutaneous absorption promoting agent and drug components.

1 Claim, No Drawings 5,120,716

PERCUTANEOUS ABSORPTION PROMOTING AGENT AND DERMATOLOGIC PREPARATION CONTAINING THE SAME

DESCRIPTION

1. Technical Field

This invention relates to a percutaneous absorption promoting agent and a dermatologic preparation containing said percutaneous absorption promoting agent. More particularly, the present invention relates to a percutaneous absorption promoting agent comprising (A) at least one anionic surfactant and one or two or more of surfactants having a nitrogen atom in the molecule other than anionic surfactants, (B) one or two or more of anionic surfactants and one or two or more of nonionic surfactants not having a nitrogen atom in the molecule, (C) one or two or more of surfactants selected from the group consisting of amphoteric surfactants and semi-polar surfactants and at least one nonionic surfactant having a nitrogen atom in the molecule, (D) one or two or more of surfactants selected from the group consisting of nonionic surfactants, amphoteric surfactants, semi-polar surfactants and cationic surfactants having a nitrogen atom in the molecule, and one or two or more of nonionic surfactants not having a nitrogen atom in the molecule, or (E) an amine oxide as the active ingredient, and dermatological preparation containing these percutaneous absorption promoting agent and drug components.

2. Background Art

Heretofore a drug component has been administered by oral administration, administration by injection, intramuscular or intravenous administration, administration to intestine or mucosa within the mouth, etc. Among them, oral administration has been most widely practiced. However, in the case of oral administration, drawbacks have occurred such that the concentration has become temporarily higher than is necessary to ensured persistence of the effect and that side effects such as stomach disorder or lack of appetite may be caused. On the other hand, although absorption is rapid in administration by injection, this must be made by an expert such as physician, etc.

Recently, dermatologic preparations by percutaneous administration have been developed to eliminate such side effects and drawbacks. However, even in such dermatologic preparations, a sufficient percutaneous absorptivity has not been yet obtained in most cases, and therefore, they are not considered satisfactory.

Further, the surface of the skin is called the skin corneum layer, which has in itself a physiological function as a barrier for protection against the penetration of foreign matter from outside of the body, and therefore, a sufficient percutaneous absorptivity can not be obtained by merely formulating a drug component in a base conventionally used in the prior art in a dermatologic preparation.

To improve this factor, various percutaneous absorption promoting agents have been proposed in recent years. For example, dimethyl sulfoxide, dimethylformamide, dimethylacetamide, methyldecyl sulfoxide, etc., are known, but these cannot be considered to have a sufficient percutaneous absorption promoting effect, safety and use feeling.

DISCLOSURE OF THE INVENTION

Accordingly, an object of the present invention is to solve the problems of the prior art as mentioned above and provide a percutaneous absorption promoting agent having an excellent percutaneous absorption promoting effect of a drug component, and further satisfactory with respect to safety and use feeling another object of the present invention is to provide a dermatologic preparation comprising the percutaneous absorption promoting agent and a drug component, which is an excellent percutaneous absorption agent promoting the effect of the drug component and further, is satisfactory with respect to safety and use feeling.

Other objects and advantages of the present invention will be apparent from the following description.

That is, the present invention provides a percutaneous absorption promoting agent for a drug component, comprising one or two or more of anionic surfactants and one or two or more of surfactants having a nitrogen atom in the molecule other than the anionic surfactants as the active ingredients and a dermatologic preparation containing a desired drug component and the above percutaneous absorption promoting agent.

The present invention also provides a percutaneous absorption promoting agent for a drug component, comprising one or two or more of amphoteric surfactants and semi-polar surfactants and one or two or more of nonionic surfactants having a nitrogen atom in the molecule as the active ingredients, and a dermatologic preparation containing a desired drug component, and the above percutaneous absorption promoting agent ingredients.

The present invention further provides a percutaneous absorption promoting agent for a drug component, comprising one or two or more of anionic surfactants and one or two or more of nonionic surfactants not having a nitrogen atom in the molecule as the active ingredients, and a dermatologic preparation containing a desired drug component, and the above percutaneous absorption promoting agent.

The present invention further provides a percutaneous absorption promoting agent for a drug component, comprising one or two or more selected from the group consisting of nonionic surfactants, amphoteric surfactants, semi-polar surfactants and cationic surfactants having a nitrogen atom in the molecule and one or two or more of nonionic surfactants not having a nitrogen atom in the molecule as the active ingredients, and a dermatologic preparation containing a desired drug component, and the above percutaneous absorption promoting agent.

The present invention further provides a percutaneous absorption promoting agent for a drug component, comprising an amine oxide as the active ingredient, and a dermatologic preparation containing a desired drug component, and the above percutaneous absorption promoting agent.

BEST MODE OF CARRYING OUT THE INVENTION

The constitution of the present invention is now described in detail.

The above anionic surfactant may include anionic surfactants having one or two or more of a carboxylic acid group, sulfonic acid group, sulfuric acid ester group, and phosphoric acid ester group, in the molecule. Those having a carboxylic acid group may include fatty acid soap, ester carboxylic acid and salts thereof, carboxylic acid salts such as condensates of amil acid and fatty acid, etc.; those having a sulfonic acid salt may include alkylsulfonic acid salts, sulfosuccinic acid, ether sulfonic acid salt, alkylallyl and alkylnaphthalene sulfonic acid salts, N-acylsulfonic acid salt, formalin condensation type sulfonic acid salts, etc.; those having a sulfuric acid ester group, may include sulfated oil, ester sulfuric acid salt, alkylsulfuric acid salt, ether sulfuric acid salt, alkylallyl ether sulfuric acid salt, amidosulfuric acid salt, etc.; those having a phosphoric acid ester group may include alkylphosphoric acid salts, amidophosphoric acid salts, ether phosphoric acid salts, alkylallyl ether phosphoric acid salts, etc. From among these, one or two or more may be selected as desired.

On the other hand, as the surfactant having a nitrogen atom in the molecule other than the anionic surfactant, there may be included nonionic surfactants, amphoteric surfactants semi-polar surfactants, cationic surfactants, etc., having a nitrogen atom in the molecule.

Examples of the nonionic surfactant having a nitrogen atom in the molecule may include fatty acid alkanolamide, polyoxyethylene fatty acid amide, esters of alkanolamine, polyoxyethylene alkylamine, etc.

Examples of the amphoteric surfactant having a nitrogen atom in the molecule may include carboxy betaine such as N,N-dimethyl-N-lauryl-N-carboxymethylammonium betaine, N,N-dimethyl-N-oleyl-N-carboxymethylammonium betaine, etc.; imidazoline derivatives such as 2-lauryl-N-carboxyethyl-N-hydroxyethylimidazolinium betaine, 2-lauryl-N-carboxymethyl-N-hydroxyethylimidazolinium betaine, etc.; aminocarboxylic acid salts such as N-cocoalkyl-$\beta$-aminopropionic acid sodium salt, N-cocoalkyl-$\beta$-iminodipropionic acid disodium salt, etc.; sulfobetaine; aminobetaine, etc.

As the semi-polar surfactant having a nitrogen atom in the molecule, there may be included amine oxides such as lauryldimethylamine oxide, stearyldimethylamine oxide, bis-(2-hydroxyethyl)laurylamine oxide, etc.

As the cationic surfactant having a nitrogen atom in the molecule, there may be included fatty acid amine salts, alkyl quaternary ammonium salts, aromatic quaternary ammonium salts, pyridinium salts, imidazolium salts, etc. From among these, one or more can be selected and used as desired.

The ratio of the above anionic surfactant to the surfactant other than the anionic surfactant having a nitrogen atom in the molecule may be preferably 20:1 1:20, more preferably 10:1 to 1:10, in terms of molar ratio.

The anionic surfactant to be used in the second embodiment of the present invention is as described above.

On the other hand, examples of the nonionic surfactant not having a nitrogen atom in the molecule to be used in the second embodiment of the present invention may include sorbitan fatty acid esters such as sorbitan monooleate, sorbitan monoisostearate, sorbitan monolaurate, sorbitan monopalmitate, sorbitan monostearate, sorbitan sesquioleate, sorbitan trioleate, penta-2-ethylhexyl acid diglycerol sorbitan, tetra-2-ethylhexyl acid diglycerol sorbitan, etc.; glycerine polyglycerine fatty acids such as mono-cotton seed oil fatty acid glycerine, mono-erucic acid glycerine, sesquioleic acid glycerine, mono-stearic acid glycerine, mono-stearic acid glycerine malic acid, etc.; propylene glycol fatty acid esters such as mono-stearic acid propylene glycol, etc; hydrophilic nonionic surfactants such as hardened caster oil derivatives, glycerine alkyl ethers, etc.; polyoxyethylene sorbitan fatty acid esters such as POE sorbitan monooleate, sorbitan monostearate, POE sorbitan monooleate, POE sorbitan tetraoleate, etc.; POE sorbitol fatty acid esters such as POE sorbitol monolaurate, POE sorbitol monooleate, POE sorbitol pentaoleate, POE sorbitol monostearate, etc.; POE glycerine fatty acid esters such as POE glycerine monostearate, POE glycerine monoisostearate, POE glycerine triisostearate, etc.; POE fatty acid esters such as POE monooleate, POE distearate, POE monodioleate, distearic acid ethylene glycol, etc.; POE alkyl ethers such as POE lauryl ether, POE oleyl ether, POE stearyl ether, POE behenyl ether, POE 2-octyldodecyl ether, POE cholestanol ether, etc.; POE alkylphenyl ethers such as POE octylphenyl ether, POE nonylphenyl ether, POE dinonylphenyl ether etc.; Pulronic type surfactants such as Pulronic, etc.; POE-POP alkyl ethers such as POE-POP cetyl ether, POE-POP 2-decyltetradecyl ether, POE-POP monobutyl ether, POE-POP hydrogenated lanolin, POE-POP glycerine ether, etc.; fatty acid esters of glycerol or polyglycerol such as diglycerine monooleate, hexaglycerine stearate, decaglycerine monolaurate, etc.; tetra POE-POP ethylenediamine condensates such as Tetronic, etc.; POE caster oil hardened caster oil derivatives such as POE caster oil, POE hardened caster oil, POE hardened caster oil monoisostearate, POE hardened caster oil triisostearate, POE hardened caster oil maleic acid, etc.; POE beeswax lanolin derivatives such as POE sorbitol beeswax, etc.; hydrophilic nonionic surfactants such as POE propylene glycol fatty acid esters, sucrose fatty acid esters, POE nonylphenylformaldehyde condensates, etc.

The ratio of the above anionic surfactant to the nonionic surfactant not having a nitrogen atom in the molecule may be preferably 20:1 to 1:20, more preferably 10:1 to 1:10, in terms of molar ratio.

As the amphoteric surfactant to be used in the third embodiment of the present invention, there may be included carboxybetaine such as N,N-dimethyl-N-lauryl-N-carboxymethylammonium betaine, N-N-dimethyl-N-oleyl-N-carboxymethylammonium betaine, etc.; imidazoline derivatives such as 2-lauryl-N-carboxyethyl-N-hydroxyethylimidazolinium betaine, 2-lauryl-N-carboxylmethyl-N-hydroxyethylimidazolinium betaine, etc.; aminocarboxylic acid salts such as N-cocoalkyl-$\beta$-aminopropionic acid sodium salt, N-cocoalkyl-$\beta$-iminodipropionic acid disodium salt, etc.; sulfobetaine, aminobetaine, etc. Examples of the above semi-polar surfactant may include amine oxides such as lauryldimethylamine oxide, stearyldimethylamine oxide, bis-(2-hydroxylethyl)laurylamine oxide, etc.

In the present invention, one or two or more selected from the group consisting of the above amphoteric surfactants and the above semi-polar surfactants may be used as desired.

On the other hand, as the nonionic surfactant having a nitrogen atom in the molecule, fatty acid alkanol amide, polyoxyethylene fatty acid amide, esters of alkanolamine, polyoxyethylenealkylamine, etc. may be included, and one or two or more may be selected as desired from among these.

The ratio of the above amphoteric surfactant and the semi-polar surfactant to the nonionic surfactant having a nitrogen atom in the molecule may be preferably 20:1 to 1:20, more preferably 10:1 to 1:10, in terms of molar ratio.

In the fourth embodiment of the present invention, the nonionic surfactant, the amphoteric surfactant, the semi-polar surfactant and/or the cationic surfactant having a nitrogen atom in the molecule are used in combination with a nonionic surfactant not having a nitrogen atom in the molecule as described above.

The ratio of one or two or more selected from the group consisting of the nonionic surfactants, the amphoteric surfactants, the semi-polar surfactants and cationic surfactants having a nitrogen atom in the molecule to the nonionic surfactant not having a nitrogen atom in the molecule may be preferably 20:1 to 1:20, preferably 10:1 to 1:10, in terms of molar ratio.

As the amine oxide to be used in the fifth embodiment of the present invention, there may be included those shown below.

(1) Amine oxide represented by the formula (I)

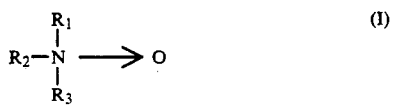

(wherein $R_1$, $R_2$ and $R_3$ represent straight or branched alkyl group or alkenyl group having 1 to 24 carbon atoms, and at least one of $R_1$, $R_2$ and $R_3$ represent straight or branched alkyl group or alkenyl group having 8 or more carbon atoms).

Specific examples of the amine oxide represented by the formula (I) may include dimethyllaurylamine oxide, dimethylmyristylamine oxide, dimethylcetylamine oxide, dimethylstearylamine oxide, dimethyloletylamine oxide, dimethylbehenylamine oxide, methyldilaurylamine oxide and the like.

(2) Dihydroxyethylalkylamine oxide represented by the formula (II)

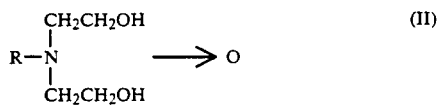

(wherein R represents straight or branched alkyl group or alkenyl group having 8 to 24 carbon atoms).

(3) Dimethylalkylpolyoxyathyl-eneamine oxide represented by the formula (III)

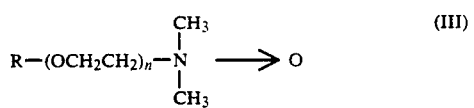

(wherein R represents a straight or branched alkyl group or alkenyl group having 8 to 24 carbon atoms, and n represents an integer of 1 to 5).

Of the above amine oxides, one or two or more may be used.

As the drug component, the pharmacological effect of which can be increased by utilization of the above percutaneous absorption promoting agent, the following drugs may be exemplified.

For example, there are steroid type anti-inflammatory agent such as predonizolone, dexamethasone, etc.; non-steroid type anti-inflammatory agent such as indomethacin, fluphenamic acid, mephenamic acid etc.; anti-histamic agents such as chlorophenylamine, diphenehydramine, promethazin, etc.; sulfur agents such as sulfur monomethoxicin, sulfur methizole, etc.; antibiotics such as penicillin, cephalosporin, chloramphenicol, streptomycin, etc.; antifungal agents such as naphthiomate, chlotrimazole, etc.; anti-malignant tumor agents such as cyclophosphamide, busulfan, actinomycin, etc.; analgesics such as morphine, codeine, nalorufin, pentazocin, aspirin, acetanilide, aminopyrin, etc.; narcotics and tranquilizers such as prostaglandins preparations, barbital, thiopental, etc.; phychopharmaceuticals such as chloropromazine, recerpine, chlorodiazeboxide, etc.; anti-Perkinson's disease agents such as chlorozoquisazone, levodopa, etc.; cardiacs such as dikitoxicin, digoxin, etc.; antiarrythmic agents such as hydrochloric acid procainamide, etc.; anti-stenocardia agents such as dipiridamol, amilnitrite, etc.; anti-hypertensives such as diazokiside, minoxyzyl, recerpine, guanitizine nitrate; UV-ray inhibitors such as para-aminobenzoate ester, etc.; melanin, formation inhibitors such as hydroquinone, arbutin, kojic acid, Vitamin C esters, para-hydroxycin namate, etc.; psoriasis PUVA therapeutics such as 8-methoxysolarene, etc.; Vitamins such as Vitamin A, Vitamin E, Vitamin C, coenzyme Q10 (Vitamin Q), etc.; hair growing agents such as cephalantin, swelthiamaline, okisendoron, etc.; hormones such as insulin, estradiol, methylteststeron, etc.; diagnostics; allergen for patch test; insecticides; secticides; humectants; corneum emoliient; hairdyes, and other drug components. Particularly as the drug component, water-soluble drug components such as indomethacin, minoxidyl, hydroquinone, arbutin, kojic acid, Vitamin C, Vitamin C ester, swelthiamaline, caphalantin, etc. can be particularly rapidly absorbed into the skin.

These drug components can be absorbed rapidly into the skin by coating on the skin when mixed with the percutaneous absorption promoting agent of the present invention. In the case of a drug component to be used for topical action, excellent effect can be exhibited by penetrating deeply into the skin, and in the case of drug component to be used for systemic action, this can also exhibit a similarly excellent effect because the drug component is migrated into the blood.

The subject to which these ingredients are applied is, of course, a human being but they can be also effectively used for other animals.

The amount of the drug component formulated may be sufficient to bring about the desired pharmacological effect, which depends also on the kind of the drug component, body weight of the patient, severity of the disease, etc.; but it may be preferably 0.001 to 5 parts by weight of the percutaneous absorption promoting agent, more preferably 0.01 to 30 parts by weight, per 1 part by weight of the drug component.

The above percutaneous absorption promoting agent may be used by suitably mixing the drug component as such, but is generally used by mixing the constituents in a base for dermatologic preparation such as cream preparation, ointment preparation, gel preparation, lotion preparation, emulsion adhesive tape, etc.

The amount of the respective constituents in that case may differ depending on the kind of the drug component, but generally the following ranges are the preferred ranges of the amount formulated. That is, the total amount of the anionic surfactant and the surfactant other than the anionic surfactant having a nitrogen atom in the molecule may be 0.001 to 10% by weight, more preferably 0.01 to 5% by weight in the dermatologic preparation, and the drug component may be 0.001 to 10% by weight, more preferably 0.01 to 5% by weight. On the other hand, for the ratio of the anionic surfactant to the surfactant having a nitrogen atom in the molecule other than anionic surfactants, the ratio as mentioned above, namely 20:1 to 1:20, preferably 10:1 to 1:10 may be applied as such.

On the other hand, the total amount formulated of the amphoteric surfactant and the semi-polar surfactant and the nonionic surfactant having a nitrogen atom in the molecule may be 0.001 to 10% by weight, more preferably 0.01 to 5% by weight in the dermatologic preparation, and the drug component may be 0.001 to 10% by weight, more preferably 0.01 to 5% by weight. For the ratio of the amphoteric surfactant and the semi-polar surfactant to the nonionic surfactant having a nitrogen atom in the molecule, the ratio as described above, namely 20:1 to 1:20, preferably 10:1 to 1:10 in terms of molar ratio may be applied as such.

The total amount of the anionic surfactant and the nonionic surfactant not having a nitrogen atom in the molecule may be 0.001 to 10% by weight, more preferably 0.01 to 5% by weight in the dermatologic preparation, while the drug component may be 0.001 to 10% by weight, more preferably 0.01 to 5% by weight. For the ratio of the anionic surfactant to the nonionic surfactant not having a nitrogen atom in the molecule, the ratio as described above, namely 20:1 to 1:20, preferably 10:1 to 1:10 in terms of molar ratio may be applied as such.

Further, the total amount formulated of one or more selected from the group consisting of nonionic surfactants, amphoteric surfactants, semi-polar surfactants and canionic surfactants having a nitrogen atom in the molecule and one or more of nonionic surfactants not having a nitrogen atom in the molecule may be 0.001 to 10% by weight, more preferably 0.01 to 5% by weight in the dermatologic preparation, and the drug component may be 0.001 to 10% by weight, more preferably 0.01 to 5% by weight. For the ratio of one or two or more selected from the group consisting of nonionic surfactants, amphoteric surfactants, semi-polar surfactants and canionic surfactants having a nitrogen atom in the molecule to one or two or more of nonionic surfactants having a nitrogen atom in the molecule, the ratio as mentioned above, namely 20:1 to 1:20, preferably 10:1 to 1:10 in terms of molar ratio may be applied as such.

Further, the amount of amine oxide formulated may be 0.0001 to 10% by weight, more preferably 0.01 to 5% by weight in the dermatologic preparation. The amount of the drug component may be 0.001 to 10% by weight, more preferably 0.01 to 5% by weight.

In the dermatologic preparation promoting the percutaneous absorption of drug component according to the present invention, it is also possible to formulate components as generally formulated in drugs, quasi drugs, cosmetic, etc. Examples of such components may include polyhydric alcohol, oil component, wax, acid, alkali, cationic surfactant, nonionic surfactant, anionic surfactant, amphoteric surfactant, powder, pigment, dye, preservative antifungal agent, anti-oxidant, UV-ray absorber, chelating agent, water-soluble polymer, montmorilonite, alcohol, solvent, flavor, etc.

More specifically, there may be included polyhydric alcohols such as glycerine, propylene glycol, etc.; oil components such as fluid paraffin, squalane, higher fatty acid, higher alcohol, etc.; organic acids such as citric acid, lactic acid, etc.; alkalis such as caustic soda, triethanolamine, etc.; anionic surfactants such as higher alkyl-sulfuric acid ester salts, higher alkylethersulfuric acid ester salts, higher fatty acid amide sulfonic acid salts, higher alkylsulfosuccinic acid salts, alkylbenzenesulfonic acid salts, acylglutamic acid salts, higher alkylphosphoric acid salts, etc.; cationic surfactants such as higher alkyl quaternary ammonium salts, fatty amine salts, alkylpyridinium salts, etc.; amphoteric surfactants such as carboxybetaine, sulfobetaine, imidazoline derivatives, etc.; polyoxyethylene alkyl ether, polyoxyethylene fatty acid amide, sorbitan fatty acid esters, fatty acid alkanolamide, polyglycerine fatty acid ester, etc.

The percutaneous absorption promoting agent and the dermatologic preparation according to the present invention have an excellent percutaneous absorption promoting effect of a drug component, and further are percutaneous absorption promoters with a good safety and use feeling.

EXAMPLES

The present invention is described in more detail by referring to Examples, but the present invention is, of course, not limited to these Examples. In the following Examples, "%" represents "% by weight", unless otherwise specifically noted.

EXAMPLE 1-1

Cream

| | | |
|---|---|---|
| (1) | Dexamethasone | 0.025% |
| (2) | Propylene glycol | 8.0 |
| (3) | Glycerine | 5.0 |
| (4) | Fluid paraffin | 1.0 |
| (5) | Diisopropyl adipate | 3.0 |
| (6) | Sodium dodecylsulfate | 0.08 |
| (7) | Dodecyldimethylamine oxide | 0.16 |
| (8) | Glycerine monofatty acid ester | 1.5 |
| (9) | Preservative | q.s. |
| (10) | Clay mineral (bentonite) | 6.0 |
| (11) | Purified water | balance |

Preparation Method

To (5) were added (1), (4), (8) and (9) and these components were dissolved and mixed by heating to 70° C. This was called composition (A). The components (6) and (7) were added to a part of (11) to be dissolved therein, followed further by an addition and mixing of the components (2) and (3). This was called composition (B). While composition (B) was stirred at a temperature maintained at 70° C, composition (A) was gradually added to effect preliminary emulsification, followed by emulsification by a homomixer.

The resultant emulsion was added to a dispersion having added and dispersed (10) in the remainder of (11) under stirring, and cooled to obtain a cream.

Comparative Example 1-1

Cream

| | | |
|---|---|---|
| (1) | Dexamethasone | 0.025% |
| (2) | Propylene glycol | 8.0 |
| (3) | Glycerine | 5.0 |
| (4) | Fluid paraffin | 1.0 |
| (5) | Diisopropyl adipate | 3.0 |
| (6) | Glycerine monofatty acid ester | 1.5 |
| (7) | Preservative | q.s. |
| (8) | Clay mineral (bentonite) | 6.0 |
| (9) | Purified water | balance |

Preparation Method

According to Example 1-1.

Test Example 1-1

For the creams prepared in Example 1-1 and Comparative Example 1-1, the vasoconstrictive action was compared.

More specifically, on the upper backs of 10 healthy human males, creams prepared in Example 1-1 and Comparative Example 1-1, and further creams of the above two kinds of creams not containing dexamethasone were respectively and randomly apportioned, applied by use of an adhesive plaster for patch test (produced by Torii Yakuhin), and plastered under sealing. After 4 hours, the adhesive plaster was peeled off, the sample removed, and judgement was conducted after further standing for 4 hours. Judgement was conducted according to the standards by achromasia phenomenon accompanied with vasoconstrictive action of steroids as "remarkable achromasia phenomenon" (score 2), "clear achromasia phenomenon" (score 1), "faint achromasia phenomenon" (score 0.5), "no change" (score 0), and an average score was determined for each base.

The results are shown in Table 1-1.

TABLE 1-1

| Base | Average score after 4 hours |
| --- | --- |
| Example | 1.7 |
| Comparative Example | 1.0 |
| System of Example from which dexamethasone is removed | 0 |
| System of Comparative Example from which dexamethasone is removed | 0 |

As apparent from Table 1-1, it can be understood that the cream of Example 1-1 had an excellent vasoconstrictive action.

EXAMPLE 1-2

Gel

| | | |
| --- | --- | --- |
| (1) | Indomethacin | 1.0% |
| (2) | Ethyl alcohol | 50.0 |
| (3) | Carboxyl vinyl polymer | 1.2 |
| (4) | Polyoxyethylene (hereinafter called POE: 40 mole) hardened caster oil | 1.5 |
| (5) | Sodium dodecylsulfate | 0.5 |
| (6) | Sodium dodecylphosphate | 0.6 |
| (7) | Sodium laurylisothionate | 0.2 |
| (8) | Dodecyldimethylamine oxide | 1.14 |
| (9) | Diethanolamide laurate | 0.2 |
| (10) | Diisopropanolamine | 0.35 |
| (11) | Purified water | balance |

Preparation Method

After (5), (6), (7), (8) and (9) were dissolved in (11), (3) was dispersed in the solution. The dispersion was added to a solution of (1) and (4) added and dissolved in (2), followed by thorough mixing. Further, to this mixture was added (10) and the mixture was stirred and mixed to obtain a gel.

Comparative Example 1-2

| | | |
| --- | --- | --- |
| (1) | Indomethacin | 1.0% |
| (2) | Ethyl alcohol | 50.0 |
| (3) | Carboxy vinyl polymer | 1.2 |
| (4) | POE hardened caster oil | 1.5 |
| (5) | Diisopropanolamine | 0.35 |
| (6) | Purified water | balance |

Preparation Method

According to Example 1-2.

Comparative Example 1-3

Commercially available ointment containing 1% indomethacin (gel-like external agent).

Test Example 1-2

For the above gel bases, the pharmacological effects were examined and compared according to the carageenin edema inhibition test.

More specifically, using 5 Wooster-strain male rats 6 weeks of age, after birth as one group, first the right rear leg volume of the rat in each group was measured by a rat rear leg footpad edema volume measuring device KM-357 (produced by Natsume Seisakusho), and then 0.2 g of a sample was applied on the right rear leg of rat. Two hours later, 0.05 ml of 1% carageenin sodium salt was subscutaneously injected at the same site, and 3 hours after the carageenin sodium salt injection, the right rear leg volume was measured to calculate foot edema inhibition according to the following formula, with the difference in the right rear leg volume before coating of the sample being the foot edema volume.

$$\text{Foot edema inhibition (\%)} = \frac{Vc - Vt}{Vc} \times 100$$

wherein $Vc$ and $Vt$ represent average edema volumes of the control group (coated with no test sample), and the group coated with test sample, respectively.

The above test results are shown in Table 1-2.

TABLE 1-2

| | Carageenin foot edema inhibition (%) |
| --- | --- |
| Example 1-2 | 53.9 |
| Comparative Example 1-2 | 11.2 |
| Comparative Example 1-3 | 8.5 |

As apparent from the table, it can be understood that the gel base of Example had an excellent carageenin edema inhibition action.

EXAMPLE 1-3

| | | |
| --- | --- | --- |
| (1) | Hydroquinone | 1.0% |
| (2) | Sodium dodecylsulfate | 0.2 |
| (3) | Dodecyldimethylamine oxide | 0.7 |
| (4) | Purified water | balance |

Preparation Method

After (2) and (3) were dissolved in (4), (1) was added and the mixture stirred and dissolved to provide a sample.

Comparative Example 1-4

| | | |
| --- | --- | --- |
| (1) | Hydroquinone | 1.0% |
| (2) | Purified water | balance |

Preparation Method

According to Example 1-3.

Comparative Example 1-5

| (1) Hydroquinone | 1.0 |
|---|---|
| (2) Urea | 5.0 |
| (3) Purified water | balance |

Preparation Method

According to Example 1-3.

Test Example 1-3

On the back skins of hairless mice, 3 mice in one group, 100 liter of a sample was plastered with Torii adhesive plaster for patch test (diameter: 1.6 cm). On the adhesive plaster was placed a sponge, which was further coated with a thin film of a rubber to which the adhesive plaster was adhered. After coating, each mouse was placed in a sealed vessel made of a plastic, with a delivery of air, and carbon dioxide discharged by breathing absorbed in a 50% methanolic solution of monoethanolamine.

After coating, the adhesive plaster at the coated portion was removed at 24 and 48 hours for measurement of the activity in the adhesive plaster Next, the coated portion was subjected to stripping with cellophane tape for 8 times, and the activity in the corneum adhered to cellophane tape was measured. Then, animals were sacrificed, the skin at the coated portion peeled off, and the activity in the skin measured. The remaining whole body was homogenated by a blender with an addition of 30 g of 0.5N aqueous sodium hydroxide, and a certain amount of the homogenate sampled for a measurement of the activity. Also, fetus and urine discharged up to a predetermined time were recovered for a measurement of the activity.

Here, the sum of the amount discharged by breathing, the amounts of fetus and urine discharged, and the amount stored in the body was defined as the percutaneous absorption amount in body. The above test results are shown in Table 1-3.

TABLE 1-3

| | Percutaneous absorption amount in body |
|---|---|
| Example 1-3 | 28.8% |
| Comparative Example 1-4 | 4.9 |
| Comparative Example 1-5 | 4.6 |
| | (after 48 hours) |

EXAMPLE 2-1

Cream

| (1) Dexamethasone | 0.025% |
|---|---|
| (2) Propylene glycol | 8.0 |
| (3) Glycerine | 5.0 |
| (4) Fluid paraffin | 1.0 |
| (5) Diisopropyl adipate | 3.0 |
| (6) Lauric acid diethanolamide | 0.6 |
| (7) N,N-dimethyl-N-lauryl-N-carboxymethylammonium betaine | 0.3 |
| (8) Glycerine monofatty acid ester | 1.5 |
| (9) Preservative | q.s. |
| (10) Clay mineral (bentonite) | 6.0 |
| (11) Purified water | balance |

Preparation Method

To (5) were added (1), (4), (8) and (9) and these components were dissolved and mixed by heating to 70° C. This was called composition (A).

The components (6) and (7) are added to a part of (11) to be dissolved therein, followed further by an addition and mixing of the components (2) and (3). This was called composition (B).

While composition (B) was stirred at a temperature maintained at 70° C., compositions (A) was gradually added to effect preliminary emulsification, followed by emulsification by a homomixer.

The resultant emulsion was added to a dispersion having added and dispersed (10) in the remainder of (11) under stirring, and cooled to obtain a cream.

Comparative Example 2-1

Cream

| (1) Dexamethasone | 0.025% |
|---|---|
| (2) Propylene glycol | 8.0 |
| (3) Glycerine | 5.0 |
| (4) Fluid paraffin | 1.0 |
| (5) Diisopropyl adipate | 3.0 |
| (6) Glycerine monofatty acid ester | 1.5 |
| (7) Preservative | q.s. |
| (8) Clay mineral (bentonite) | 6.0 |
| (9) Purified water | balance |

Preparation Method

According to Example 2-1.

Test Example 2-1

For the creams prepared in Example 2-1 and Comparative Example 2-1, the vasoconstrictive action was compared as in Test Example 1-1.

The results are shown in Table 2-1.

TABLE 2-1

| Base | Average score after 4 hours |
|---|---|
| Example 2-1 | 1.7 |
| Comparative Example 2-1 | 1.0 |
| System of Example 2-1 from which dexamethasone is removed | 0 |
| System of Comparative Example 2-1 from which dexamethasone is removed | 0 |

As apparent from Table 2-1, it can be understood that the cream of Example 2-1 have an excellent vasoconstrictive action.

EXAMPLE 2-2

Gel

| (1) Indomethacin | 1.0% |
|---|---|
| (2) Ethyl alcohol | 50.0 |
| (3) Carboxyl vinyl polymer | 1.2 |
| (4) Polyoxyethylene (hereinafter called P.O.E.) hardened caster oil | 1.5 |
| (5) Lauryldimethylamine oxide | 0.6 |
| (6) P.O.E. (15 mole) oleyl amine | 0.8 |

-continued

| | | |
|---|---|---|
| (7) N,N-dimethyl-N-lauryl-N-sulfomethylammonium betaine | 1.0 | |
| (8) Diethanolamine laurate | 0.35 | |
| (9) Diisopropanolamine | 0.35 | |
| (10) Purified water | balance | |

Preparation Method

After (5), (6), (7) and (8) were dissolved in (10), (3) was well dispersed in the solution. The dispersion was added to a solution of (1) and (4) added and dissolved in (2), followed by thorough mixing. Further, to this mixture was added (9) and the mixture stirred and mixed to obtain a gel.

Comparative Example 2-2

| | |
|---|---|
| (1) Indomethacin | 1.0% |
| (2) Ethyl alcohol | 50.0 |
| (3) Carboxyl vinyl polymer | 1.2 |
| (4) POE hardened caster oil | 1.5 |
| (5) Diisopropanolamine | 0.35 |
| (6) Purified water | balance |

Preparation Method

According to Example 2-2.

Comparative Example 2-3

Commercially available ointment containing 1% indomethacin (gel-like external agent).

Test Example 2-2

For the above gel-like bases, the pharmacological effects were examined and compared as in Test Example 1-2 according to the carageenin edema inhibition test.

The above test results are shown in Table 2-2.

TABLE 2-2

| | Carageenin foot edema inhibition (%) |
|---|---|
| Example 2-2 | 50.8 |
| Comparative Example 2-2 | 11.2 |
| Comparative Example 2-3 | 8.5 |

As apparent from the table, it can be understood that the gel base of Example had an excellent carageenin edema inhibition action.

EXAMPLE 2-3

| | |
|---|---|
| (1) Hydroquinone | 1.0% |
| (2) Coconut fatty acid diethanolamide | 0.8 |
| (3) Dodecyldimethylamine oxide | 0.5 |
| (4) Purified water | balance |

Preparation Method

After (2) and (3) were dissolved in (4), (1) was added, and the mixture stirred and dissolved to provide a sample.

Comparative Example 2-4

| | |
|---|---|
| (1) Hydroquinone | 1.0% |
| (2) Purified water | balance |

Preparation Method

According to Example 2-3.

Comparative Example 2-4

| | |
|---|---|
| (1) Hydroquinone | 1.0% |
| (2) Urea | 5.0 |
| (3) Purified water | balance |

Preparation Method

According to Example 2-3.

Test Example 2-3

For the samples obtained above, the percutaneous absorption amounts were determined as in Test Example 1-3.

The above test results are shown in Table 2-3.

TABLE 2-3

| | Percutaneous absorption amount |
|---|---|
| Example 2-3 | 26.8% |
| Comparative Example 2-4 | 4.9 |
| Comparative Example 2-5 | 4.6 |
| | (after 48 hours) |

EXAMPLE 3-1

Cream

| | |
|---|---|
| (1) Dexamethasone | 0.025% |
| (2) Propylene glycol | 8.0 |
| (3) Glycerine | 5.0 |
| (4) Fluid paraffin | 1.0 |
| (5) Diisopropyl adipate | 3.0 |
| (6) Sodium myristylsulfate | 2.5 |
| (7) Sobitan monooleate | 1.0 |
| (8) Glycerine monofatty acid ester | 1.5 |
| (9) Preservative | q.s. |
| (10) Clay mineral (bentonite) | 6.0 |
| (11) Purified water | balance |

Preparation Method

To (5) were added (1), (4), (8) and (9) and these components were dissolved and mixed by heating to 70° C. This was called composition (A). The components (6) and (7) were added to a part of (11) to be dissolved therein, followed further by an addition and mixing of components (2) and (3). This was called composition (B). While composition (B) was stirred at a temperature maintained at 70° C., composition (A) was gradually added to effect preliminary emulsification, followed by emulsification by a homomixer.

The resultant emulsion was added to a dispersion having added and dispersed (10) in the remainder of (11) under stirring, and cooled to obtain a cream.

Comparative Example 3-1

Cream

| | |
|---|---|
| (1) Dexamethasone | 0.025% |

|  |  |  |
|---|---|---|
| (2) Propylene glycol | 8.0 | |
| (3) Glycerine | 5.0 | |
| (4) Fluid paraffin | 1.0 | |
| (5) Diisopropyl adipate | 3.0 | |
| (6) Glycerine monofatty acid ester | 1.5 | |
| (7) Preservative | q.s. | |
| (8) Clay mineral (bentonite) | 6.0 | |
| (9) Purified water | balance | |

Preparation Method

According to Example 3-1.

Test Example 3-1

For the creams prepared in Example 3-1 and Comparative Example 3-1, the vasoconstrictive action was compared as in Test Example 1-1.

The results are shown in Table 3-1.

TABLE 3-1

| Base | Average score after 4 hours |
|---|---|
| Example 3-1 | 1.4 |
| Comparative Example 3-1 | 1.0 |
| System of Example 3-1 from which dexamethasone is removed | 0 |
| System of Comparative Example 3-1 from which dexamethasone is removed | 0 |

As apparent from the table, it can be understood that the cream of Example 3-1 had an excellent vasoconstrictive action.

EXAMPLE 3-2

Gel

| (1) Indomethacin | 1.0% |
|---|---|
| (2) Ethyl alcohol | 50.0 |
| (3) Carboxyl vinyl polymer | 1.2 |
| (4) Polyoxyethylene (40 mole addition) hardened castor oil | 1.5 |
| (5) Sodium dodecylsulfate | 0.7 |
| (6) Sodium monolaurylphosphate | 0.6 |
| (7) Sodium laurylisothionate | 0.7 |
| (8) POE sorbitan monostearate | 2.3 |
| (9) Sucrose fatty acid ester | 1.5 |
| (10) Diisopropanolamine | 0.35 |
| (11) Purified water | balance |

Preparation Method

After (5), (6), (7), (8) and (9) were dissolved in (11), (3) was dispersed in the solution. The dispersion was added to a solution of (1) and (4) added and dissolved in (2), followed by thorough mixing. Further, to this mixture was added (10) and the mixture was stirred and mixed to obtain a gel.

Comparative Example 3-2

| (1) Indomethacin | 1.0% |
|---|---|
| (2) Ethyl alcohol | 50.0 |
| (3) Carboxyl vinyl polymer | 1.2 |
| (4) Polyoxyethylene (40 mole addition) hardened castor oil | 1.5 |
| (5) Diisopropanolamine | 0.35 |
| (6) Purified water | balance |

Preparation Method

According to Example 3-2.

Comparative Example 3-3

Commercially available ointment containing 1% indomethacin (gel-like external agent).

Test Example 3-2

For the above gel bases, the pharmacological effects were examined and compared as in Test Example 1-2 according to the carageenin edema inhibition test.

The above test results are shown in Table 3-2.

TABLE 3-2

|  | Carageenin foot edema inhibition (%) |
|---|---|
| Example 3-2 | 48.3 |
| Comparative Example 3-2 | 11.2 |
| Comparative Example 3-3 | 8.5 |

As apparent from the table, it can be understood that the gel base of Example 3-2 had an excellent carageenin edema inhibition action.

EXAMPLE 3-3

| (1) Hydroquinone | 1.0% |
|---|---|
| (2) Sodium N-lauroyl glutamate | 1.2 |
| (3) Polyoxyethylene (15 mole addition) stearyl ether | 1.6 |
| (4) Purified water | balance |

Preparation Method

After (2) and (3) were dissolved in (4), (1) was added and the mixture stirred and dissolved to provide a sample.

Comparative Example 3-4

| (1) Hydroquinone | 1.0% |
|---|---|
| (2) Purified water | balance |

Preparation Method

According to Example 3-3.

Comparative Example 3-5

| (1) Hydroquinone | 1.0% |
|---|---|
| (2) Urea | 5.0 |
| (3) Purified water | balance |

Preparation Method

According to Example 3-3.

Test Example 3-3

For the samples obtained above, the percutaneous absorption amounts were determined as in Test Example 1-3.

The above test results are shown in Table 3-3.

TABLE 3-3

| | Percutaneous absorption amount |
|---|---|
| Example 3-3 | 21.8% |
| Comparative Example 3-4 | 4.9 |
| Comparative Example 3-5 | 4.6 |

(after 48 hours)

EXAMPLE 4-1

Cream

| | | |
|---|---|---|
| (1) | Dexamethasone | 0.025% |
| (2) | Propylene glycol | 8.0 |
| (3) | Glycerine | 5.0 |
| (4) | Fluid paraffin | 1.0 |
| (5) | Diisopropyl adipate | 3.0 |
| (6) | Fatty acid alkanolamide | 1.8 |
| (7) | Sorbitan monooleate | 1.0 |
| (8) | Glycerine monofatty acid ester | 1.5 |
| (9) | Preservative | q.s. |
| (10) | Clay mineral (bentonite) | 6.0 |
| (11) | Purified water | balance |

Preparation Method

To (5) were added (1), (4), (8) and (9) and these components were dissolved and mixed by heating to 70° C. This was called composition (A). The components (6) and (7) were added to a part of (11) to be dissolved therein, followed further by an addition and mixing of components (2) and (3). This was called composition (B). While composition (B) was stirred at a temperature maintained at 70° C., composition (A) was gradually added to effect preliminary emulsification, followed by emulsification by a homomixer.

the resultant emulsion was added to a dispersion having added and dispersed (10) in the remainder of (11) under stirring, and cooled to obtain a cream.

Comparative Example 4-1

Cream

| | | |
|---|---|---|
| (1) | Dexamethasone | 0.025% |
| (2) | Propylene glycol | 8.0 |
| (3) | Glycerine | 5.0 |
| (4) | Fluid paraffin | 1.0 |
| (5) | Diisopropyl adipate | 3.0 |
| (6) | Glycerine monofatty acid ester | 1.5 |
| (7) | Preservative | q.s. |
| (8) | Clay mineral (bentonite) | 6.0 |
| (9) | Purified water | balance |

Preparation Method

According to Example 4-1.

Test Example 4-1

For the creams prepared in Example 4-1 and Comparative Example 4-1, the vasoconstrictive action was compared as in Test Example 1-1. The results are shown in Table 4-1.

TABLE 4-1

| Base | Average score after 4 hours |
|---|---|
| Example 4-1 | 1.5 |
| Comparative Example 4-1 | 1.0 |
| System of Example 4-1 from which dexamethasone is removed | 0 |

TABLE 4-1-continued

| Base | Average score after 4 hours |
|---|---|
| System of Comparative Example 4-1 from which dexamethasone is removed | 0 |

As apparent from the table, it can be understood that the cream of Example 4-1 had an excellent vasoconstrictive action.

EXAMPLE 4-2

Gel

| | | |
|---|---|---|
| (1) | Indomethacin | 1.0% |
| (2) | Ethyl alcohol | 50.0 |
| (3) | Carboxyl vinyl polymer | 1.2 |
| (4) | Polyoxyethylene (40 mole addition) hardened caster oil | 1.5 |
| (5) | Diethanolamide laurate | 1.5 |
| (6) | Lauryldimethylamine oxide | 1.0 |
| (7) | Lauryl betaine | 0.5 |
| (8) | POE sorbitan monostearate | 1.14 |
| (9) | Sucrose fatty acid ester | 0.2 |
| (10) | Diisopropanolamine | 0.35 |
| (11) | Purified water | balance |

Preparation Method

After (5), (6), (7), (8) and (9) were dissolved in (11), (3) was dispersed in the solution. The dispersion was added to a solution (1) and (4) added and dissolved in (2), followed by thorough mixing. Further, to this mixture was added (10) and the mixture stirred and mixed to obtain a gel.

Comparative Example 4-2

| | | |
|---|---|---|
| (1) | Indomethacin | 1.0% |
| (2) | Ethyl alcohol | 50.0 |
| (3) | Carboxy vinyl polymer | 1.2 |
| (4) | Polyoxyethylene (40 mole addition) hardened caster oil | 1.5 |
| (5) | Diisopropanolamine | 0.35 |
| (6) | Purified water | balance |

Preparation Method

According to Example 4-2.

Comparative Example 4-3

Commercially available ointment containing 1% indomethacin (gel-like external agent).

Test Example 4-2

For the above gel bases, the pharmacological effects were examined and compared as in Test Example 1-2 according to the carageenin edema inhibition test.

The above test results are shown in Table 4-2.

TABLE 4-2

| | Carageenin foot edema inhibition (%) |
|---|---|
| Example 4-2 | 49.1 |
| Comparative Example 4-2 | 11.2 |
| Comparative Example 4-3 | 8.5 |

As apparent from the table, it can be understood that the gel base of Example 4-2 had an excellent carageenin edema inhibition action.

EXAMPLE 4-3

| | |
|---|---|
| (1) Hydroquinone | 1.0% |
| (2) Distearyldimethyl ammonium chloride | 0.5 |
| (3) Triglycerine monolaurate | 1.5 |
| (4) Purified water | balance |

Preparation Method

After (2) and (3) were dissolved in (4), (1) was added and the mixture stirred and dissolved to provide a sample.

Comparative Example 4-4

| | |
|---|---|
| (1) Hydroquinone | 1.0% |
| (2) Purified water | balance |

Preparation Method

According to Example 4-3.

Comparative Example 4-5

| | |
|---|---|
| (1) Hydroquinone | 1.0% |
| (2) Urea | 5.0 |
| (3) Purified water | balance |

Preparation Method

According to Example 4-3.

Test Example 4-3

For the samples obtained above, the percutaneous absorption amounts were determined as in Test Example 1-3.

The above test results are shown in Table 4-3.

TABLE 4-3

| | Percutaneous absorption amount |
|---|---|
| Example 4-3 | 23.7% |
| Comparative Example 4-4 | 4.9 |
| Comparative Example 4-5 | 4.6 |
| | (after 48 hours) |

EXAMPLES 5-1–5-5

Drug Permeability Test

A drug permeability test was conducted for amine oxide, which is the product of the present invention.

Pharmaceutical samples comprising the following composition were prepared.

| | |
|---|---|
| (1) Hydroquinone | 1.0% |
| (2) Test substance | 0.1% |
| (3) Ethanol | 20.0 |
| (4) Purified water | balance |

Preparation Method

After (1) and (2) were dissolved in (3), (4) was added and mixed to provide a sample.

Test Substance

Tests were conducted for the following test substances.

(A) Amine oxide insoluble or slightly soluble in water

EXAMPLE 5-1

Dimethylstearylamine oxide

EXAMPLE 5-2

Dimethylbehenylamine oxide

EXAMPLE 5-3

Dihyroxyethylstearylamine oxide (B) Water-soluble amine oxide

EXAMPLE 5-4

Dimethyllaurylamine oxide

EXAMPLE 5-5

Dimethylmyristylamine oxide

Comparative Example 5-1

| | |
|---|---|
| (1) Hydroquinone | 1.0% |
| (2) Ethanol | 20.0 |
| (3) Purified water | balance |

Preparation Method

According to Examples 5-1–5-5.

Test Example 5-1

For an evaluation of the percutaneous absorption promoting effect of a drug with the test substance, a drug permeability test was conducted by in vitro diffusion cell, using the enucleated skin of a hairless mouse. As the diffusion cell device, a vertical film type 2-compartment cell with a diffusion area of 2 $cm^2$ was employed. The whole skin layer at the back of a 10 to 15 weeks old male hairless mouse was enucleated and mounted on a diffusion cell. In the cell compartment on the medicament sample side, 2 ml of a medicament sample was placed, and 2 ml of a phosphate buffer phisiological saline (pH 7.2) was placed in the cell compartment on the receptor side, and the whole cell maintained at 32° C. in a thermostat tank while gently stirring both phases. After 24 hours, the receptor solution was sampled and the amount of the drug permeated by high performance chromatography to the receptor side quantitated. The results are represented in drug permeability (%). The results are shown in Table 5-1.

TABLE 5-1

| | Test substance | Drug permeability | Effect |
|---|---|---|---|
| Example 5-1 | Dimethylstearylamine oxide | 44.0 | |
| Example 5-2 | Dimethylbehenylamine oxide | 28.6 | |
| Example 5-3 | Dihydroxyethylstearylamine oxide | 30.5 | |
| Example 5-4 | Dimethyllaurylamine oxide | 9.4 | |
| Example 5-5 | Dimethylmyristylamine oxide | 11.8 | |
| Comparative | — | 2.1 | — |

TABLE 5-1-continued

| Test substance | Drug permeability | Effect |
|---|---|---|
| Example 5-1 | | |

As apparent from the table, the percutaneous absorption promoting agent of the present invention had an excellent skin permeability promoting effect of a drug, and particularly, it can be understood that insoluble or slightly soluble amine oxides had excellent effects.

Drug Percutaneous Absorption Test

EXAMPLE 5-6

| | | |
|---|---|---|
| (1) [$^{14}$C]Hydroquinone | 1.0% | |
| (2) Dimethylstearylamine oxide | 0.1 | |
| (3) Ethanol | 20.0 | |
| (4) Purified water | balance | |

Preparation Method

After (1) and (2) were dissolved in (3), (4) was added and mixed to provide a sample.

Comparative Example 5-2

| | | |
|---|---|---|
| (1) [$^{14}$C]Hydroquinone | 1.0% | |
| (2) Ethanol | 20.0 | |
| (3) Purified water | balance | |

Preparation Method

According to Example 5-6.

Comparative Example 5-3

| | | |
|---|---|---|
| (1) [$^{14}$C]Hydroquinone | 1.0% | |
| (2) Urea | 5.0 | |
| (3) Ethanol | 20.0 | |
| (4) Purified water | balance | |

Preparation Method

After (1) was dissolved in (3), a solution of (2) dissolved in (4) was added and mixed to provide a sample.

Test Example 5-2

On the back skin of hairless mice, 3 mice in one group, 100 μl of a sample was plastered with a Torii adhesive plaster for patch test (diameter: 1.6 cm). On the adhesive plaster was placed a sponge, which was further coated with a thin film of a rubber to which the adhesive plaster was adhered. After coating, the mouse was placed in a sealed vessel made of a plastic, with a delivery of air, and carbon dioxide discharged by breathing was absorbed in a 50% methanolic solution of monoethanolamine.

After coating, the adhesive plaster at the coated portion was removed at 24 and 48 hours for measurement of the radioactivity in the adhesive plaster. Next, the coated portion was subjected to stripping with cellophane tape for 8 times, and the radioactivity in the corneum adhered to cellophane tape measured. Then, the animals were sacrificed, the skin at the coated portion peeled off, and the radioactivity in the skin measured. The remaining whole body was homogenated by a blender with an addition of 30 g of 0.5N aqueous sodium hydroxide, and a certain amount of the homogenate was sampled for measurement of the radioactivity. Also, fetus and urine discharged up to a predetermined time were recovered for measurement of the radioactivity. Here, the sum of the amount discharged by breathing, the amounts of fetus and urine discharged, and the amount stored in the body was defined as the percutaneous adsorption amount in the body. The above test results are shown in Table 5-2.

TABLE 5-2

| | Percutaneous absorption amount in body |
|---|---|
| Example 5-6 | 35.5% |
| Comparative Example 5-2 | 4.1 |
| Comparative Example 5-3 | 4.9 |
| | (after 48 hours) |

As apparent from the table, it can be understood that the percutaneous absorption promoting agent of the present invention had an excellent effect of absorption promotion of a drug.

EXAMPLE 5-7

Cream

| | | |
|---|---|---|
| (1) Dexamethasone | 0.025% | |
| (2) Propylene glycol | 8.0 | |
| (3) Glycerine | 5.0 | |
| (4) Fluid paraffin | 1.0 | |
| (5) Diisopropyl adipate | 3.0 | |
| (6) Dimethylstearylamine oxide | 5.0 | |
| (7) Glycerine monofatty acid ester | 1.5 | |
| (8) Preservative | q.s. | |
| (9) Clay mineral (bentonite) | 6.0 | |
| (10) Purified water | balance | |

Preparation Method

To (6) were added (1), (4), (5), (7) and (8) and these compounds were dissolved and mixed by heating to 70° C. This was called composition (A). The components (2) and (3) were added to a part of (10). This was called composition (B). While composition (B) was stirred at a temperature maintained at 70° C., composition (A) was gradually added to effect preliminary emulsification, followed by emulsification by a homomixer. The resultant emulsion was added to a dispersion having added and dispersed (9) in the remainder of (10) under stirring, and cooled to obtain a cream.

Comparative Example 5-4

Cream

| | | |
|---|---|---|
| (1) Dexamethasone | 0.025% | |
| (2) Propylene glycol | 8.0 | |
| (3) Glycerine | 5.0 | |
| (4) Fluid paraffin | 1.0 | |
| (5) Diisopropyl adipate | 3.0 | |
| (6) Glycerine monofatty acid ester | 1.5 | |
| (7) Preservative | q.s. | |
| (8) Clay mineral (bentonite) | 6.0 | |
| (9) Purified water | balance | |

Preparation Method

According to Example 5-7.

Test Example 5-3

For the creams prepared in Example and Comparative Example, the vasoconstrictive action was compared as in Test Example 1-1.

The results are shown in Table 5-3.

TABLE 5-3

| Base | Average score after 4 hours |
|---|---|
| Example 5-7 | 1.8 |
| Comparative Example 5-4 | 0.9 |
| System of Example 5-7 from which dexamethasone is removed | 0 |
| System of Comparative Example 5-4 from which dexamethasone is removed | 0 |

As apparent from the table, it can be understood that the cream of Example 5-7 had an excellent vasoconstrictive action.

EXAMPLE 5-8

Gel

| | | |
|---|---|---|
| (1) | Indomethacin | 1.0% |
| (2) | Ethyl alcohol | 50.0 |
| (3) | Carboxy vinyl polymer | 1.2 |
| (4) | Polyoxyethylene (40) hardened castor oil | 1.5 |
| (5) | Dimethylbehenylamine oxide | 1.0 |
| (6) | Diisopropanolamine | 0.35 |
| (7) | Purified water | balance |

Preparation Method

After (1), (4) and (5) were dissolved in (2), (3) dissolved in (7) was added, followed by thorough mixing. Further, to this mixture was added (6) and the mixture stirred and mixed to obtain a gel.

Comparative Example 5-5

| | | |
|---|---|---|
| (1) | Indomethacin | 1.0% |
| (2) | Ethyl alcohol | 50.0 |
| (3) | Carboxy vinyl polymer | 1.2 |
| (4) | Polyoxyethylene (40) hardened castor oil | 1.5 |
| (5) | Diisopropanolamine | 0.35 |
| (6) | Purified water | balance |

Preparation Method

According to Example 5-8.

Comparative Example 5-6

Commercially available ointment containing 1% indomethacin (gel-like external agent).

Test Example 5-4

For the above gel bases, the pharmacological effects were examined and compared as in Test Example 1-2 according to the carageenin edema inhibition test.

The above test results are shown in Table 5-4.

TABLE 5-4

| | Carageenin foot edema inhibition % |
|---|---|
| Example 5-8 | 56.1 |
| Comparative Example 5-5 | 12.0 |
| Comparative Example 5-6 | 10.8 |

As apparent from the table, it can be understood that the gel base of Example 5-8 has an excellent carageenin edema inhibition action.

Test Example 6-1

The percutaneous absorption promotion effect of drugs with the test substances shown in Table 6-1 were evaluated as in Test Example 5-1.

TABLE 6-1

| | Test substance | | Drug | Drug permeability (%) |
|---|---|---|---|---|
| Example 6-1 | Sodium dodecylsulfate<br>Dodecylaminoacetic acid betaine | 0.2%<br>0.5% | Arbutin<br>0.3% | 39% |
| Example 6-2 | Sodium dodecylsulfate<br>Dodecylaminoacetic acid betaine | 0.2%<br>0.5% | Minoxidyl<br>0.3% | 32% |
| Example 6-3 | Sodium dodecylsulfate<br>Dodecylaminoacetic acid betaine | 0.2%<br>0.5% | Kojic acid<br>0.3% | 40% |
| Example 6-4 | Laurylimidazoliniumbetaine<br>Lauryldiethanolamide | 0.1%<br>0.5% | Arbutin<br>0.3% | 27% |
| Example 6-5 | Stearyldimethylamine oxide | 0.5% | Arbutin<br>0.3% | 34% |
| Comparative Example 6-1 | — | | Arbutin<br>0.3% | 1% |

In the table, numerical values (%) in the column of test substance and drug show the concentrations in aqueous solution.

As apparent from the results in the above table, it can be understood that the test substances (percutaneous absorption promoting agent) of Examples 6-1–6-5 according to the present invention have a remarkably excellent skin permeability promoting effect of drugs.

We claim:

1. A dermatological preparation comprising (i) 0.001–10% by weight of at least one drug component selected from the group consisting of dexamethasone, indomethacin, minoxidyl, hydroquinone, arbutin, kojic acid, naphthiomate, Vitamin C, 8-methoxysolarene, Vitamin C ester, swelthiamaline, and cephalantin and (ii) 0.001–10% by weight of a percutaneous absorption promoting agent comprising (A) at least one anionic surfactant and (B) at least one surfactant having a nitrogen atom in the molecule other than anionic and cationic surfactants as the active ingredients, the mole ratio of the components (A)/(B) being 20/1 to 1/20.

* * * * *